United States Patent
Konishi et al.

(10) Patent No.: US 9,435,008 B2
(45) Date of Patent: Sep. 6, 2016

(54) INDIUM RECOVERY METHOD

(75) Inventors: Yasuhiro Konishi, Sakai (JP); Norizo Saito, Sakai (JP); Arumi Higashi, Sakai (JP)

(73) Assignee: Osaka Prefecture University Public Corporation, Osaka (JP)

( * ) Notice: Subject to any disclaimer, the term of this patent is extended or adjusted under 35 U.S.C. 154(b) by 8 days.

(21) Appl. No.: 14/126,835

(22) PCT Filed: Aug. 9, 2012

(86) PCT No.: PCT/JP2012/070329
§ 371 (c)(1),
(2), (4) Date: Dec. 16, 2013

(87) PCT Pub. No.: WO2013/024782
PCT Pub. Date: Feb. 21, 2013

(65) Prior Publication Data
US 2014/0144292 A1    May 29, 2014

(30) Foreign Application Priority Data
Aug. 12, 2011    (JP) .................. 2011-176936

(51) Int. Cl.
C22B 7/00      (2006.01)
C22B 58/00     (2006.01)
C22B 3/24      (2006.01)
C12N 1/20      (2006.01)
B09B 3/00      (2006.01)
C12P 3/00      (2006.01)

(52) U.S. Cl.
CPC .............. *C22B 58/00* (2013.01); *B09B 3/0016* (2013.01); *C12N 1/20* (2013.01); *C12P 3/00* (2013.01); *C22B 3/24* (2013.01); *C22B 7/007* (2013.01); *Y02P 10/234* (2015.11)

(58) Field of Classification Search
CPC .......... C22B 7/007; C22B 58/00; C22B 3/24; C12N 1/20
See application file for complete search history.

(56) References Cited

U.S. PATENT DOCUMENTS

2002/0153521 A1*  10/2002  Hattori et al. .................... 257/1
2005/0155870 A1    7/2005  Koyama et al.
2008/0038188 A1    2/2008  Ohnishi et al.

FOREIGN PATENT DOCUMENTS

CN    101701291    *  5/2010
JP    2002-201025 A    7/2002
(Continued)

OTHER PUBLICATIONS

Konishi et al. Japanese patent No. 2011026701 A published Feb. 10, 2011. Machine translation.*
(Continued)

*Primary Examiner* — George Wyszomierski
*Assistant Examiner* — Tima M McGuthry Banks
(74) *Attorney, Agent, or Firm* — Studebaker & Brackett PC (57) ABSTRACT

According to the present invention, there is provided an indium recovery method for recovering indium from an indium-containing product, including a leaching step of allowing indium to leach into an aqueous hydrochloric acid solution by hydrothermal leaching using the aqueous hydrochloric acid solution as a leaching agent from the indium-containing product to obtain a leachate composed of an aqueous hydrochloric acid solution containing indium, and a separating step of adding a microbe for adsorbing In ions to the leachate to separate indium from the leachate.

7 Claims, 6 Drawing Sheets

(56) References Cited

FOREIGN PATENT DOCUMENTS

| JP | 2009-102679 A | | 5/2009 |
|---|---|---|---|
| JP | 2009155717 A | * | 7/2009 |
| JP | 2009-191309 A | | 8/2009 |
| JP | 2011-026701 A | | 2/2011 |
| JP | 4843491 B2 | | 12/2011 |

OTHER PUBLICATIONS

Wang et al. Chinese patent No. 101701291 A published May 5, 2010. Machine translation.*
Watanabe et al. Japanese patent No. 2009155717 A published Jul. 16, 2009. Machine translation.*
Konishi et al. Japanese Patent No. 2011026701 A published Feb. 10, 2011. Full Human translation.*
The extended European search report issued by the European Patent Office on Jan. 21, 2015, which corresponds to European Patent Application No. 12823304.6-1362 and is related to U.S. Appl. No. 14/126,835.
T.Ogi et al.; "Recovery of indium from aqueous solutions by the Gram-negative bacterium Shewanella algae"; Biochemical Engineering Journal, vol. 63, Elsevier B.V., Apr. 15, 2012; pp. 129-133.
T.Honma et al.; "Material Collection from Liquid Crystal Display Wasted Panels", Sharp Gihoh 92 (2005), pp. 17-22.
M.Tsujiguchi et al.; "Rare Metal Recovery and Recycling in Consumer-electronics Production"; Haikibutu Shigen Junkan Gakkaishi 20 (2009), pp. 77-84.
K.Inoue et al.; "Recovery of Indium from Spent Panel of Liquid Crystal Display Panels", Kagaku Kogaku Ronbunshu 34 (2008), pp. 282-286.
S.Schiewer et al.; "Biosorption Processes for Heavy Metal Removal", Environmental Microbe-Metal Interactions (2000), pp. 329-362.
N.Das; "Recovery of precious metals through biosorption—A review"; Hydrometallurgy, 103 (210); pp. 180-189.
J.Cui et al.; "Metallurgical recovery of metals from electronic waste: A review"; Journal of Hazardous Materials, 158 (2008); pp. 228-256.
A.Higashi et al.; "Recovery of Indium by Biosorption and Its Application to Recycling of Waste Liquid Crystal Display Panel"; Journal of the Japan Institute of Metals, Nov. 1, 2011, vol. 75; pp. 620-625.
T.Ogi et al.; "Recovery of indium from aqueous solutions by the Gram-negative baterium Shewanella algae"; Biochemical Engineering Journal, vol. 63, Elsevier B.V., Apr. 15, 2012; pp. 129-133.
Y.Konishi; "Rare Metal no Recycle Saishin Doko Biseibutsu o Riyo suru Rare Metal no Shigen Junkan System"; Sangyo to Kankyo, Mar. 1, 2011, vol. 40; pp. 69-72.

* cited by examiner

(Cell concentration:6.7 × 10¹⁵cells/m³, adsorption operating time:120 min)

FIG.6

(Solution pH 2.6)

INDIUM RECOVERY METHOD

TECHNICAL FIELD

The present invention relates to a method for recovering indium from an indium-containing product.

BACKGROUND ART

Indium is an essential rare metal for the production of ITO (indium-tin oxide) constituting a transparent electrode film material used for an LCD (a liquid crystal panel display). The reserves of indium as a natural resource are unevenly distributed and located in China. Under circumstances in which indium as a natural resource is substantially monopolized by China, Japan is a major indium-consuming country where the demand for the ground metal accounts for over 80% of the global demand (yearly).

In our country, most of indium is used for the production of ITO for an LCD, and, due to upsizing in an LCD and the rapid expansion of the market, there has been a sharp increase in demand therefor. In recent years, with regard to scrap generated in the production process such as a used ITO target material and a deposit on a tool for sputtering, the recycling has proceeded. However, it is thought that indium recovery has not been performed against home electric appliances including a used LCD and a failed panel generated in an LCD factory, and recovering indium from an indium-containing product such as the used LCD and the failed LCD is becoming an important issue. In particular, since an LCD television and the like are added to the list of objective items for Home Appliance Recycling Law, establishing a technology for recycling indium from a used LCD and the like is an important issue from the aspects of securing a stable supply of resources such as rare metals and attaining the volume reduction and detoxification of inorganic waste.

There have been some reports on the study relating to indium recovery from a used LCD product. An adsorption/desorption method using an ion exchange resin against an LCD leachate leaching with hydrochloric acid has been proposed by an LCD manufacturer (NPD 1: T. Honma and T. Muratani: Sharp Gihoh 92 (2005) 17-22, NPD 2: M. Tsujiguchi and H. Doi: Haikibutu Shigen Junkan Gakkaishi 20 (2009) 77-84). Moreover, basic research on subjecting a used LCD panel to leaching by means of an inorganic acid and then adsorbing and separating indium by means of a reagent impregnated resin (prepared by allowing an ion exchange resin to be impregnated with a reagent for solvent extraction) using the leachate as an object has been conducted (NPD 3: K. Inoue, M. Nishiura, H. Kawakita, K. Ohto, and H. Harada: Kagaku Kogaku Ronbunshu 34 (2008) 282-286).

In these conventional methods, there remain issues relating to efficient indium recovery from a dilute solution containing negligible amounts of indium, the economic efficiency in an indium recovery process, the necessity of the wastewater treatment in a downstream step thereof and the like.

Under such circumstances, it is thought that biosorption (organic adsorption) utilizing an inexpensive bio-material such as a microorganism as an adsorbing agent, as a method for removing a metal from a dilute solution, becomes a promising approach as a method for recovering indium from a used LCD. In biosorption, a phospholipid and lipopolysaccharides that exist on the cell surface layer of a microorganism (a carboxyl group, a phosphate group and the like as functional groups) act as ion exchangers and metal ions are removed from the liquid phase.

For the purpose of treating wastewater containing harmful metals and purifying an aquatic environment polluted with heavy metals, numerous research findings relating to the adsorption and separation of various harmful metals have been reported up to the present time (NPD 4: S. Schiewer and B. Volesky: Biosorption Processes for Heavy Metal Removal, (Environmental Microbe-Metal Interactions, D. R. Lovley (ed.), ASM Press, Washington, D.C., 2000) pp. 329-362). Moreover, biosorption utilizing various microorganisms, as a method for separating and recovering a noble metal from a dilute solution, has been attracting attention (NPD 5: N. Das: Hydrometallurgy, 103 (2010) 180-189, NPD 6: J. Cui and L. Zhang: J. Hazard. Mater. 158 (2008) 228-256).

With regard to biosorption of indium that is a rare metal, PTD 1 (Japanese Patent Laying-Open No. 2011-26701) discloses a method for recovering indium, gallium and tin by treatment with an iron-reducing bacterium from a metal-containing material containing indium, gallium and tin. However, in particular, there is no disclosure about a method for selectively recovering indium.

Moreover, PTD 2 (Japanese Patent No. 4843491) discloses a method for recovering indium by means of an anion exchange resin from an acid solution composed mainly of hydrochloric acid containing indium. However, the anion exchange resin has no selectivity for indium because the resin adsorbs all anions, including a chloride ion derived from hydrochloric acid in an FPD leachate. Moreover, although a hydrochloric acid solution with a high concentration (3.5%:1.2 M) is used as a leaching agent and the leaching is performed over a long period of 60 minutes, for example, under relatively moderate conditions (80° C., atmospheric pressure) in Example 1, the recovery percentage is as low as about 55% (see FIG. 9). Moreover, since the pH of the leachate is less than or equal to 1, there is also a problem that tin dissolves in the leachate and a separating step for tin is required.

CITATION LIST

Patent Document

PTD 1: Japanese Patent Laying-Open No. 2011-26701
PTD 2: Japanese Patent No. 4843491

Non Patent Document

NPD 1: T. Honma and T. Muratani: Sharp Gihoh 92 (2005) 17-22
NPD 2: M. Tsujiguchi and H. Doi: Haikibutu Shigen Junkan Gakkaishi 20 (2009) 77-84
NPD 3: K. Inoue, M. Nishiura, H. Kawakita, K. Ohto, and H. Harada: Kagaku Kogaku Ronbunshu 34 (2008) 282-286
NPD 4: S. Schiewer and B. Volesky: Biosorption Processes for Heavy Metal Removal, (Environmental Microbe-Metal Interactions, D. R. Lovley (ed.), ASM Press, Washington, D.C., 2000) pp. 329-362
NPD 5: N. Das: Hydrometallurgy, 103 (2010) 180-189
NPD 6: J. Cui and L. Zhang: J. Hazard. Mater. 158 (2008) 228-256

SUMMARY OF INVENTION

Technical Problem

The present invention is aimed at providing a method capable of efficiently recovering indium from an indium-containing product (a used LCD and the like).

Solution to Problem

The present invention is directed to an indium recovery method for recovering indium from an indium-containing product, comprising a leaching step of allowing indium to leach into an aqueous hydrochloric acid solution by hydrothermal leaching using the aqueous hydrochloric acid solution as a leaching agent from the indium-containing product to obtain a leachate composed of an aqueous hydrochloric acid solution containing indium, and a separating step of adding a microbe for adsorbing In ions to the leachate to separate indium from the leachate.

It is preferred that the concentration of the aqueous hydrochloric acid solution be 0.05 to 0.5 M. Moreover, it is preferred that the temperature of the aqueous hydrochloric acid solution be maintained at 110 to 130° C. in the leaching step. It is preferred that the pressure condition in the leaching step be 0.143 to 0.270 MPa. It is preferred that the treating time in the leaching step be 3 to 60 minutes.

It is preferred that the pH of the leachate before adding or after adding the microbe for adsorbing In ions be 2.2 to 3.0 in the separating step.

It is preferred that the microbe for adsorbing In ions be *Shewanella algae* or *Shewanella oneidensis*.

It is preferred that the microbe for adsorbing In ions be subjected to a drying treatment or be calcined after the separating step to recover indium.

Advantageous Effects of Invention

According to the present invention, it is possible to efficiently recover indium from an indium-containing product (a used LCD and the like). In particular, by allowing indium to undergo biosorption and to separate at high selectivity from a dilute solution containing negligible amounts of indium, it is possible to efficiently recover indium from a used indium-containing product.

DESCRIPTION OF EMBODIMENTS

<Leaching Step>

At the time of In leaching from a used LCD, an aqueous hydrochloric acid solution with a concentration of 3M (3000 mol/m$^3$) is used as a leaching agent in a known method (Patent Document 2). The reason why such an aqueous hydrochloric acid solution with a high concentration is used is because it is generally considered that the higher the hydrochloric acid concentration is, the more increased the amount of In allowed to leach out is. However, in the case where a 3M aqueous hydrochloric acid solution is used as a leaching agent in an upstream step of the adsorption operation by means of cells of *S. algae*, it follows that high concentration hydrochloric acid is left behind in the leachate and a pH adjustment step that consumes a high concentration alkali solution is required as a pretreatment of the biosorption operation. Besides, the leachate is diluted by the addition of the alkali solution and it follows that the In (III) concentration is lowered and the amount of waste liquid generated after the In (III) recovery is increased.

Taking these problems into consideration, it is desirable to use a dilute aqueous hydrochloric acid solution as a leaching agent used at the time of allowing In to leach out from an indium-containing product (a used LCD and the like), but it is thought that the recovery rate of indium is lowered when the concentration of the aqueous hydrochloric acid solution is merely lowered.

By employing hydrothermal leaching as a method for allowing In to leach out from an indium-containing product in view of solving the problems, the present inventors have found that efficient recovery of In is possible even in the case of using a dilute aqueous hydrochloric acid solution. In this context, hydrothermal leaching in the present invention refers to a method of adding a ground product of an indium-containing product and the like to a leaching agent (an aqueous hydrochloric acid solution) in a high-temperature and high-pressure state and allowing indium to leach into the leaching agent.

That is, in the leaching step of the present invention, by hydrothermal leaching using a 0.05 to 0.5M aqueous hydrochloric acid solution as a leaching agent, indium is allowed to leach into the aqueous hydrochloric acid solution from the indium-containing product. The concentration of the aqueous hydrochloric acid solution is more preferably about 0.1M. By using such an aqueous hydrochloric acid solution with a lower concentration than the conventional one, the above-stated problem in a treatment for the leachate after the leaching step is eliminated. In this connection, the leachate means an aqueous hydrochloric acid solution containing indium obtained by allowing indium to leach into an aqueous hydrochloric acid solution.

Specifically, for example, by grinding an indium-containing product and adding the ground product to a 0.05 to 0.5M aqueous hydrochloric acid solution heated to a predetermined temperature, it is possible to allow indium to leach into the aqueous hydrochloric acid solution. The temperature of the aqueous hydrochloric acid solution in the leaching step is preferably 110 to 130° C., more preferably 115 to 125° C. In this case, it is possible to suppress tin from leaching out and to selectively recover indium into the leachate.

In this connection, the pressure condition in the leaching step is adjusted depending on the temperature condition and is preferably adjusted depending on the temperature condition within a preferred range of 0.143 to 0.270 MPa.

The treating time in the leaching step is preferably 3 to 60 minutes, more preferably 5 to 10 minutes, from the viewpoint of recovery efficiency of indium in the whole recovery work.

Although the indium-containing product is not particularly limited as long as it is a product containing indium, examples thereof include a used LCD. It is preferred that the indium-containing product be a product containing indium and aluminum and at least one selected from the group consisting of Cu, Sn, Sr, Mg and Si. In this way, according to the present invention, it is possible to selectively recover indium from a product containing indium and metals other than indium. In this connection, in this case, the leaching step becomes a step of allowing indium and aluminum and at least one selected from the group consisting of Cu, Sn, Sr, Mg and Si to leach into an aqueous hydrochloric acid solution by hydrothermal leaching using the aqueous hydrochloric acid solution as a leaching agent from the indium-containing product to obtain a leachate composed of an aqueous hydrochloric acid solution containing indium and aluminum and at least one selected from the group consisting of Cu, Sn, Sr, Mg and Si.

<Separating Step>

After the leaching step, a microbe for adsorbing In ions is added to the leachate to separate indium from the leachate. In this context, specifically, separating indium means, for example, allowing indium to be adsorbed on the surface of a microbe for adsorbing In ions.

(Microbe for Adsorbing In Ions)

The microbe for adsorbing In ions used in the present invention is a microbe capable of adsorbing indium in a solution on its cell without demonstrating reducing action among microbes that are supplied with electrons from an electron donor and reduce metal ions. Such a microbe for adsorbing In ions is exemplified by the genus *Geobacter* (type species: *Geobacter metallireducens*, ATCC (American Type Culture Collection) 53774 strain), the genus *Desulfuromonas* (type species: *Desulfuromonas palmitatis*: ATCC51701 strain), the genus *Desulfuromusa* (typical species: *Desulfuromusa kysingii*: DSM (Deutsche Sammlung von Mikroorganismen and Zellkulturen) 7343 strain), the genus *Pelobacter* (type species: *Pelobacter venetianus*: ATCC2394 strain), the genus *Shewanella* (*Shewanella algae*: ATCC51181 strain (hereinafter, abbreviated as "*S. algae*"), *Shewanella oneidensis*: ATCC700550 strain (hereinafter, abbreviated as "*S. oneidensis*")), the genus *Ferrimonas* (*Ferrimonas balearica*: DSM9799 strain), the genus *Aeromonas* (*Aeromonas hydrophila*: ATCC15467 strain), the genus *Sulfurospirillum* (type species: *Sulfurospirillum barnesii*: ATCC700032 strain), the genus *Wolinella* (type species: *Wolinella succinogenes*: ATCC29543 strain), the genus *Desulfovibrio* (type species: *Desulfovibrio desulfuricans*: ATCC29577 strain), the genus *Geothrix* (type species: *Geothrix fermentans*: ATCC700665 strain), the genus *Deferribacter* (type species: *Deferribacter thermophilus*: DSM14813 strain), the genus *Geovibrio* (type species: *Geovibrio ferrireducens*: ATCC51996 strain), the genus *Pyrobaculum* (type species: *Pyrobaculum islandicum*: DSM4184 strain), the genus *Thermotoga* (type species: *Thermotoga maritima* DSM3109 strain), the genus *Archaeoglobus* (type species: *Archaeoglobus fulgidus*: ATCC49558 strain), the genus *Pyrococcus* (type species: *Pyrococcus furiosus*: ATCC43587 strain), the genus *Pyrodictium* (type species: *Pyrodictium abyssi*: DSM6158 strain) and the like.

With regard to the microbe for adsorbing In ions used in the present invention, the proliferation and maintenance thereof need only to be performed using a culture medium suitable for the microbe. For example, *S. algae* can be proliferated and maintained by batch-culturing using a ferric citrate culture medium (ACTT No. 1931) with a pH of 7.0 in which sodium lactate (32 mol/m$^3$) as an electron donor and the Fe (III) ion (56 mol/m$^3$) as an electron acceptor are contained. Although the salt from which the iron ion originates is a citrate in this example, it needs only to be appropriately selected according to the kinds of a culture medium to be used and a microbe for adsorbing In ions to be used. With regard to the microbe for adsorbing In ions that grows under either of an anaerobic condition and an aerobic condition such as *S. algae*, from the point of culture efficiency, it is preferred to perform the culture under an aerobic condition.

Among the microbes for adsorbing In ions used in the present invention, a particularly preferred one is *S. algae* or *S. oneidensis*. By using the cell of *S. oneidensis* as an adsorbing agent, In (III) ions can be separated as in the case of *S. algae*.

On the cell surface layer of *Shewanella algae* that is a gram-negative bacterium, a protein and the like exist (V. R. Phoenix, A. A. Korenevsky, F. G. Ferris, Y. A. Gorby and T. J. Beveridge: Current Microbiol. 55 (2007) 152-157), and it is thought that these biological materials effectively act for the adsorption of metal ions. In the present invention, the cell of *S. algae* is used as an adsorbing agent for In (III) ions. In this connection, *S. algae* is known as a metal ion-reducing bacterium and has a function capable of reducing Fe (III) ions and noble metal ions (Au (III), Pd (II) and Pt (IV)) by employing an organic acid salt (a lactic acid salt or the like) as an electron donor under an anaerobic environment (J. R. Lloyd and L. E. Macaskie: Adv. Appl. Microbiol. 53 (2003) 85-128, Y. Konishi, T. Tsukiyama, K. Ohno, N. Saitoh, T. Nomura and S. Nagamine: Hydrometallurgy 81 (2006) 24-29, Y. Konishi, K. Ohno, N. Saitoh, T. Nomura, S. Nagamine, H. Hishida, Y. Takahashi and T. Uruga: J. Biotechnol. 128 (2007) 648-653, Y. Konishi, T. Tsukiyama, N. Saitoh, T. Nomura, S. Nagamine, Y. Takahashi and T. Uruga: J. Biosci. Bioeng. 103 (2007) 568-571, Y. Konishi, T. Tsukiyama, T. Tachimi, N. Saitoh, T. Nomura and S. Nagamine: Electrochimica Acta 53 (2007) 186-192, and K. Tamaoki, N. Saito, T. Ogi, T. Nomura and Y. Konishi: Kagaku Kogaku Ronbunshu 36 (2010) 288-292).

Since the standard electrode potential of indium (III) ($In^{3+}+3e \Leftrightarrow In$; $-0.34$ V) is considerably lower than the standard electrode potential of any of these metal ions and the like (for example, $Fe^{3+}+e \Leftrightarrow Fe^{2+}$; 0.77 V), it is difficult to reduce the In (III) ion by the action of *S. algae*. As such, the cell of *S. algae* is used as an adsorbing agent to separate In (III) ions.

The cell concentration in a leachate after adding the microbe for adsorbing In ions to the leachate is preferably $1.0 \times 10^{14}$ to $1.0 \times 10^{17}$ cells/m$^3$, more preferably $1.0 \times 10^{15}$ to $1.5 \times 10^{16}$ cells/m$^3$. In this connection, the microbe for adsorbing In ions is usually added to a leachate in a state of viable cells.

It is preferred that the pH of a leachate before adding or after adding the microbe for adsorbing In ions be adjusted to lie within the range of 2.2 to 3.0 by adding an alkaline material such as sodium hydroxide and potassium hydroxide to the leachate. It is more preferred that the pH of a leachate after adding the microbe for adsorbing In ions be adjusted to lie within the range of 2.2 to 3.0. In the case where the pH is adjusted to lie within such a range, only In (III) ions can be further selectively adsorbed and separated by means of the microbe for adsorbing In ions, and it is possible to further enhance the recovery rate of indium in the indium recovery method according to the present invention.

After the separating step, the microbe for adsorbing In ions into the interior of which indium is incorporated and the microbe for adsorbing In ions onto the surface of which indium is bonded can be, for example, subjected to a drying treatment or calcined to finally recover indium. In the case of drying the microbe for adsorbing In ions, for example, by allowing microbial cells to stand for about 12 hours in a drying apparatus at about 50° C., the water in the microbial cells may be evaporated to recover them as In concentrates. Furthermore, in order to remarkably reduce the quantity of microbial cells, the microbial cells may be subjected to a heat treatment in a high-temperature furnace at about 800° C. to recover In.

EXAMPLES

Hereinafter, the present invention will be described in more detail with reference to examples, but the present invention is not limited thereto. It should be noted that a cell suspension of *S. algae* cultivated as follows was used in the following examples.

(Microorganism Culture and Preparation of Cell Suspension)

As a microbe for adsorbing In ions, *S. algae* of ATCC 51181 strain furnished from ATCC (American Type Culture Collection) was prepared. The culture of *S. algae* was performed at room temperature using a TSB (Tryptone Soya Broth) liquid culture medium (pH 7.2) under an aerobic environment. The batch-culturing was performed for 12 to 16 hours, after which microbial cells were harvested by centrifuging (15,880×g) the culture liquid and washed with ion-exchanged water. The washed cells were resuspended in ion-exchanged water to prepare a cell suspension of *S. algae*.

Example 1

In the present example, an adsorption experiment of In ions in an aqueous $InCl_3$ solution with cells of *S. algae* was performed by a batch process.

Specifically, the cell suspension of *S. algae* was mixed with each of aqueous $InCl_3$ solutions of three kinds of concentrations, and an adsorption experiment of In ions was performed. In these liquid mixtures, their initial concentrations of In (III) ions were 0.08, 0.40 and 0.80 mol/m$^3$, each of their pHs was set to 2.9, and each of their cell concentrations was set to $4.0 \times 10^{15}$ cells/m$^3$. In this connection, in the present example, all the operations were performed under an aerobic environment (at room temperature and atmospheric pressure).

After the adsorption experiment was started (after the cell suspension was mixed), an aliquot of the liquid mixture was sampled at the end of a predetermined time (3 minutes, 30 minutes and 60 minutes). In order to stop the adsorption of In (III) ions to microbial cells, the liquid mixture sampled was immediately filtered through a filter (with a pore diameter of 0.2 nm, made of a cellulose mixed ester) to separate cells of *S. algae* from the liquid phase. Then, the In (III) ion concentration in the liquid phase was measured using a multi-type ICP emission spectroscopic analyzer (ICPE-9000, Shimadzu Corporation).

Moreover, as sterile controls, with regard to aqueous $InCl_3$ solutions with the same concentrations as the initial concentrations of In (III) ions in the three kinds of liquid mixtures (aqueous $InCl_3$ solutions with which a cell suspension is not mixed), the measurement of the In (III) ion concentration at the end of a predetermined time (0 minute, 3 minutes, 30 minutes and 60 minutes) after the preparation of the aqueous $InCl_3$ solutions was performed. The measurement results of the present example are shown in FIG. 1.

Figure 1:
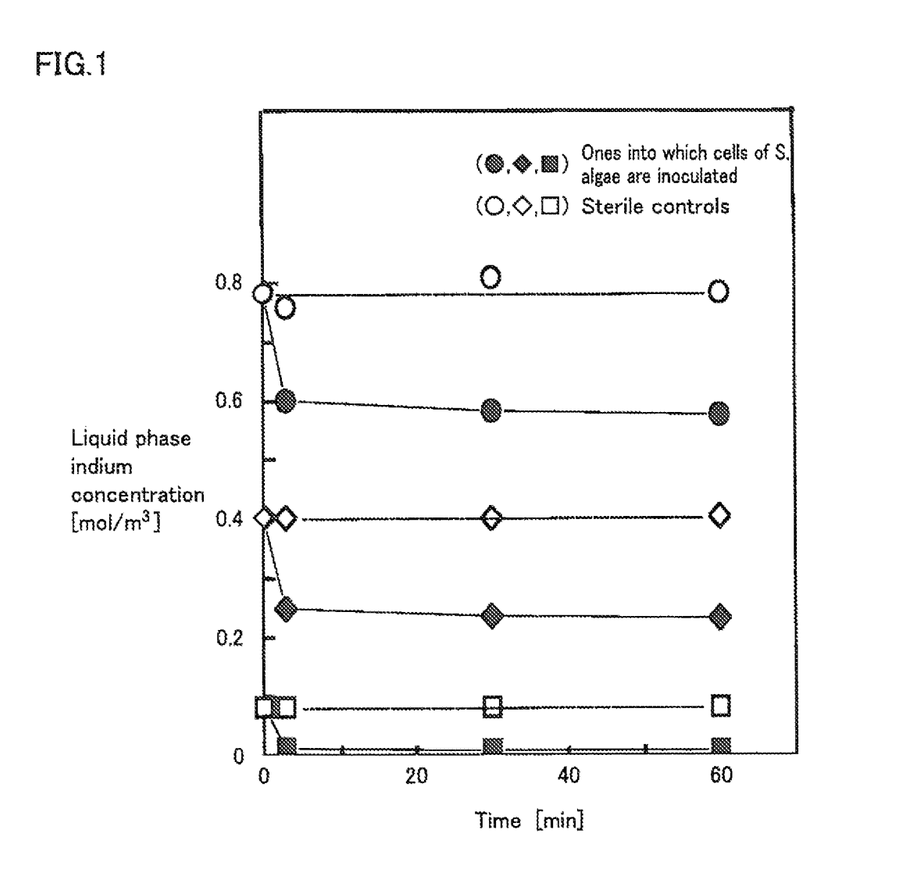
FIG. 1 is a graph showing the experimental results of Example 1.

The results shown in FIG. 1 reveal that while the concentration of In (III) ions in the liquid phase decreases with the lapse of time in the presence of cells of *S. algae*, the biosorption phenomenon of In (III) ions occurs. Moreover, it can also be seen that In (III) ions are quickly adsorbed by cells of *S. algae* and the adsorption equilibrium is attained by a batch process operation performed over a period of 30 minutes or less. Thus, it has become apparent that the cell of *S. algae* (ATCC51181 strain) is an effective biosorption agent against dilute $InCl_3$ solutions with initial In (III) ion concentrations of 0.08, 0.40 and 0.80 mol/m$^3$. In this connection, in sterile controls in which a cell suspension of cells of *S. algae* was not mixed, the In (III) concentration is kept unchanged.

Example 2

In the present example, an experiment for investigating the influence, which the solution pH has, of each of In (III) ions, Sn (IV) ions and Al (III) ions on the biosorption was performed. That is, with regard to each of an aqueous $InCl_3$ solution, an aqueous $SnCl_4$ solution and an aqueous $AlCl_3$ solution, an adsorption experiment with cells of *S. algae* (ATCC 51181 strain) was performed. By allowing the pH of liquid mixtures (ones prepared by mixing each of the three kinds of aqueous solutions of ions with a cell suspension) to be changed, the relationship between a balanced value of the adsorption percentage of each of In (III) ions, Sn (IV) ions and Al (III) ions and the pH of the liquid mixture was investigated.

Figure 2:
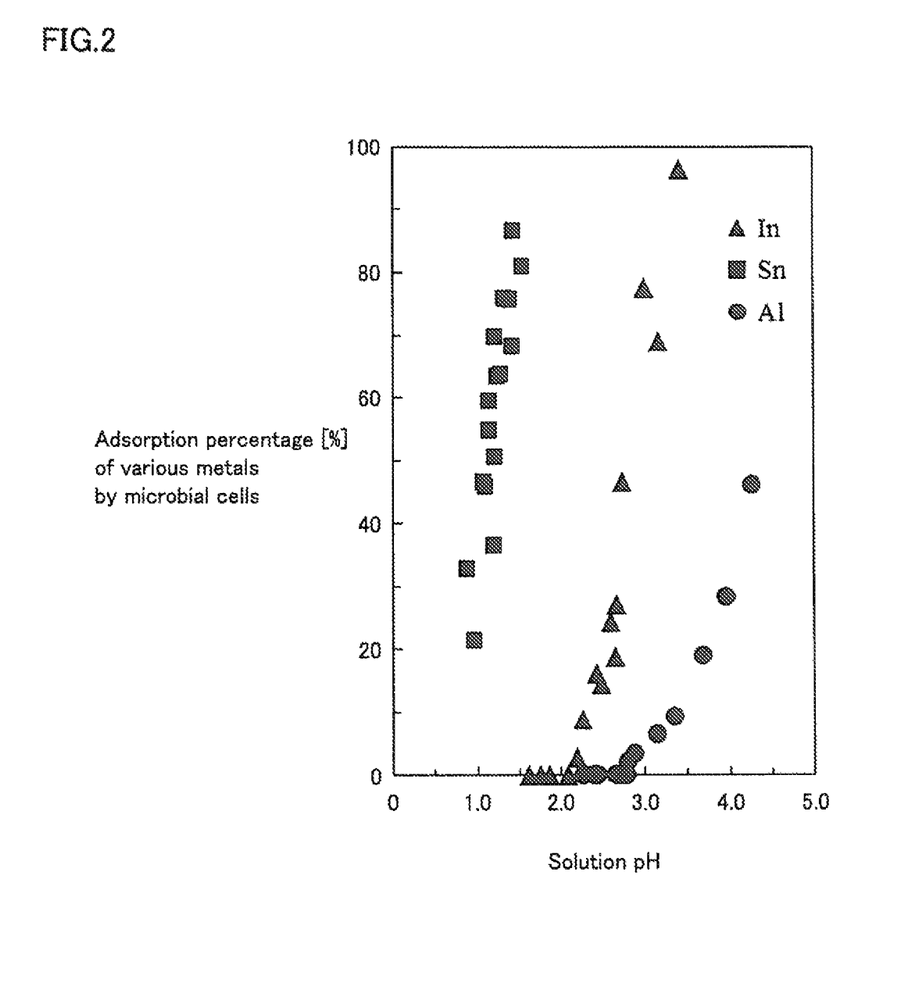
FIG. 2 is a graph showing the experimental results of Example 2.

Specifically, the cell suspension of *S. algae* was mixed with each of an aqueous $InCl_3$ solution, an aqueous $SnCl_4$ solution and an aqueous $AlCl_3$ solution, and an adsorption experiment for each of In (III) ions, Sn (IV) ions and Al (III) ions was performed by a batch process. Moreover, the pH was appropriately changed as shown in FIG. 2. In these liquid mixtures, each of their initial concentrations of In (III) ions was 0.50 mol/m$^3$, and each of their cell concentrations was set to $4.0 \times 10^{15}$ cells/m$^3$. In this connection, in the present example, all the operations were performed under an aerobic environment (at room temperature and atmospheric pressure).

After the cell suspension was mixed (after the adsorption experiment was started), an aliquot of the liquid mixture was sampled at the end of 60 minutes. This is because it is thought that the adsorption percentage at this point has reached a balanced value. Afterward, each metal ion concentration in the liquid mixture was measured in the same manner as that in Example 1 to determine the cell concentration in the liquid mixture. Furthermore, in the present example, the decreasing percentage of each metal ion concentration to the initial concentration (each metal ion concentration in a liquid mixture immediately after subjected to a pH adjustment) in the liquid mixture is calculated and the decreasing percentage is defined as the adsorption percentage of each metal ion. As the experimental results of the present example, the relationship between the adsorption percentage of each of In (III) ions, Sn (IV) ions and Al (III) ions and the pH of the liquid mixture is shown in FIG. 2.

As shown in FIG. 2, it can be seen that the adsorption of In (III) ions by cells of *S. algae* occurs at a solution pH greater than or equal to 2.2, the In (III) adsorption percentage significantly increases with an increase in pH, and the In (III) adsorption percentage reaches nearly 100% at a solution pH of 3.5. In this way, the solution pH is an important operational factor in controlling the biosorption behavior of In (III) ions.

Moreover, it can be seen that when comparing adsorption behaviors of each metal ion, the adsorption of each of Sn (IV), In (III) and Al (III) is allowed to become significant even in a lower pH range in this order. As shown in FIG. 2, the preferred pH value at which the cell of *S. algae* acts as an adsorbing agent is a pH value greater than or equal to 1.0 for the Sn (IV) ion that has the largest valence number, a pH value greater than or equal to 2.2 (more preferably a pH value greater than or equal to 2.5) for the In (III) ion, and a pH value greater than or equal to 2.9 for the Al (III) ion. Thus, it is thought that the selection of the solution pH is of key importance in order to attain the selective adsorption of In (III) ions by cells of *S. algae* in the metal ion mixed solution.

Example 3

In the present example, an experiment for investigating the influence, which the cell concentration has, of indium on the biosorption was performed. That is, with regard to an aqueous $InCl_3$ solution, an adsorption experiment with cells of *S. algae* (ATCC 51181 strain) was performed. By allowing the cell concentration in a liquid mixture after mixing the cell suspension with an aqueous $InCl_3$ solution to be changed in a range of $2.0 \times 10^{15}$ to $10.0 \times 10^{15}$ cells/m$^3$, the relationship between an adsorption percentage of In (III) ions (a balanced value) and the cell concentration in a liquid mixture was investigated.

Specifically, each of cell suspensions of *S. algae* of three kinds of concentrations was mixed with an aqueous $InCl_3$ solution, and the adsorption experiment for In (III) ions was performed by a batch process. In these liquid mixtures, their cell concentrations of *S. algae* were $2.0 \times 10^{15}$, $4.0 \times 10^{15}$ and $10.0 \times 10^{15}$ cells/m$^3$ respectively, each of their initial concentrations of In (III) ions was 0.50 mol/m$^3$, and each pH was 3.0. In this connection, in the present example, all the operations were performed under an aerobic environment (at room temperature and atmospheric pressure).

After the cell suspension was mixed with the aqueous $InCl_3$ solution (after the adsorption experiment was started), an aliquot of the liquid mixture was sampled at the end of 60 minutes. Afterward, the In (III) ion concentration in the liquid mixture was measured in the same manner as that in Example 1 to determine the cell concentration in the liquid mixture. Furthermore, the decrease in In (III) ion concentration relative to the initial concentration (In (III) ion concentration in a liquid mixture immediately after subjected to a pH adjustment) in the liquid mixture was calculated in the same manner as that in Example 2, and from the decrease in In (III) ion concentration, the amount of In (III) ions adsorbed by microbial cells was calculated. As the experimental results of the present example, the relationship between the amount of In (III) ions adsorbed and the cell concentration in the liquid mixture is shown in FIG. 3.

Figure 3:
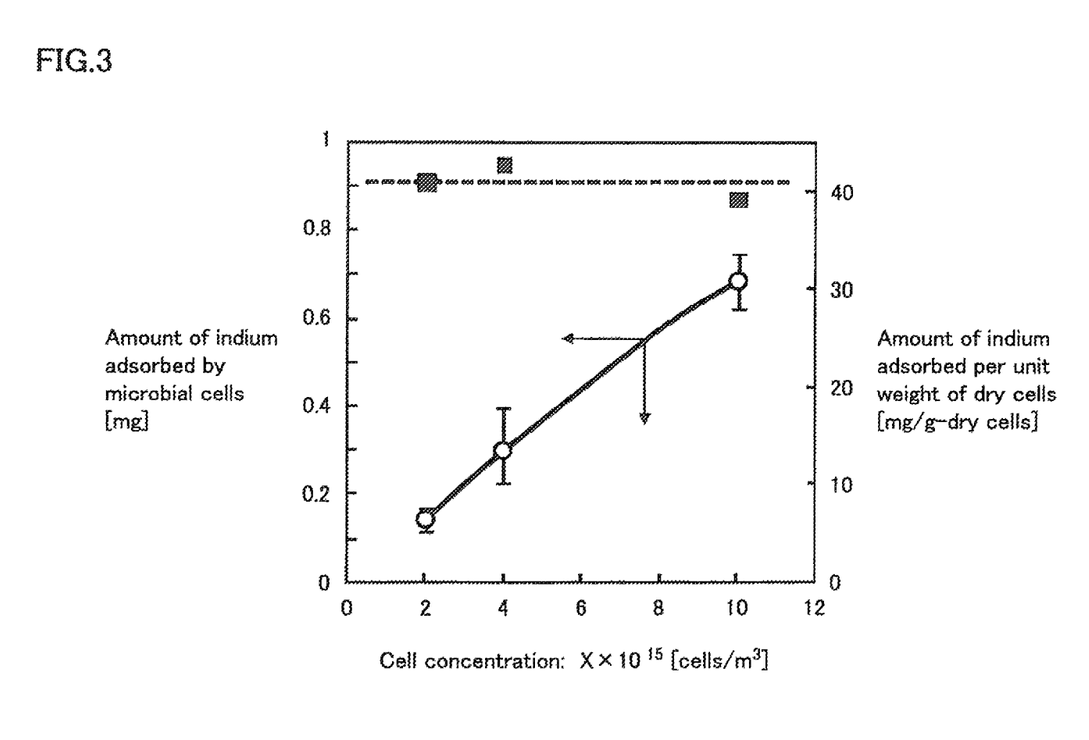
FIG. 3 is a graph showing the experimental results of Example 3.

As shown by points of outlined circle in FIG. 3, with an increase in cell concentration, the total amount of In (III) adsorbed to cells of *S. algae* and separated from the liquid phase increases (see the numerical value on the left side in FIG. 3). The results show that the higher the cell concentration (the number of cells inoculated into the solution) in the present example becomes, the more increased the total amount of In (III) adsorbed is. That is, in the range of the cell concentration in the present example, it can be seen that the recovery efficiency of indium is enhanced by using a cell suspension with a high concentration.

In this connection, in the range allowing the cell concentration to be $2.0 \times 10^{15}$ to $10.0 \times 10^{15}$ cells/m$^3$, the amount of In (III) adsorbed which is expressed in terms of an amount per unit weight of dry cells was calculated, whereupon as shown by points of filled square in FIG. 3, regardless of the cell concentration, the amount was kept at a nearly constant value (41±2 mg/g-dry cells) (see the numerical value on the right side). This also reveals that in the range of the cell concentration in the present example ($2.0 \times 10^{15}$ to $10.0 \times 10^{15}$ cells/m$^3$), the amount of In (III) adsorbed per cell is not decreased and the total amount of In (III) adsorbed increases in proportion to the cell concentration.

In this connection, the weight of dry cells is calculated on the basis of a stoichiometric relationship between the number of cells and the weight of dry cells in which $8.58 \times 10^{12}$ cells/g-dry cells holds true for cells subjected to drying at 50° C. for 12 hours (K. Tamaoki, N. Saito, T. Ogi, T. Nomura and Y. Konishi: Kagaku Kogaku Ronbunshu 36 (2010) 288-292). That is, the whole number of cells is calculated by multiplying each cell concentration by the volume of the liquid mixture (15 cm$^3$), and from the number of cells, the weight of dry cells is calculated. Then, the amount of In (III) adsorbed per unit weight is calculated by dividing the total amount of In (III) adsorbed and separated by the weight of dry cells.

(Enrichment of Intracellular Indium Adsorbed)

From the amount of In (III) adsorbed (41±2 mg/g-dry cells) described above, the In concentration in the dry cell is calculated to be 3.9% by weight (39000 ppm). Since the initial In (III) concentration in the starting solution employed in the adsorption experiment is 0.5 mol/m$^3$ (57 ppm), it has become apparent that a concentrate in which the In (III) concentration is increased by about 680 times (39000/57≈684) can be recovered by the adsorption operation for In (III) ions by means of cells of *S. algae* and the drying operation (50° C., 12 hours) for wet cells. When the quantity of the In-containing cell itself can be reduced, the In concentration factor can be further increased.

Apart from the present example, in order to remarkably reduce the quantity of microbial cells, the In-containing cell was placed in a melting pot, and this was subjected to a heat treatment in a high-temperature furnace at 800° C. As a result of allowing most of the microbial cells to be burned, it was found that a compound with an In content ratio of 62% by weight (620000 ppm) is formed. In this case, the In concentration rate relative to the starting solution (the initial In (III) concentration is 0.9 mol/m$^3$ (103.3 ppm)) attains about 6000 (620000/103.3=6002).

Example 4

Based on the experimental results achieved by an aqueous single metal salt solution described above, using an aqueous binary metal salt solution as an object, an adsorption experiment by means of cells of *S. algae* (ATCC 51181 strain) was performed and an experiment for investigating the adsorption behavior of each metal was performed.

In the present example, in view of the metal concentration in an LCD leachate described below, an In (III)-Al (III) solution (an aqueous solution containing In (III) ions at 0.08 mol/m$^3$ (9.2 ppm) and Al (III) ions at 0.90 mol/m$^3$ (24 ppm)) was used as an aqueous binary metal salt solution.

The cell suspension of *S. algae* was mixed with the aqueous binary metal salt solution, and an adsorption experiment for In (III) ions and Al (III) ions was performed by a batch process. The pHs of the liquid mixtures were adjusted to 2.7, 2.8 and 3.3. In this connection, even in the present example, all the operations were performed under an aerobic environment (at room temperature and atmospheric pressure).

After the cell suspension was mixed with the aqueous binary metal salt solution (after the adsorption experiment was started), an aliquot of the liquid mixture was sampled at the end of each of 3 minutes, 30 minutes, 60 minutes and 120 minutes. Afterward, the concentration of each metal ion in the liquid mixture was measured in the same manner as that in Example 1. In the adsorption experiment, each of the cell concentrations in the liquid mixtures was $4.0 \times 10^{15}$ cells/m$^3$. As the experimental results of the present example, the change in the concentration of each of In (III) ions and Al (III) ions with time is shown in FIG. 4.

Figure 4:
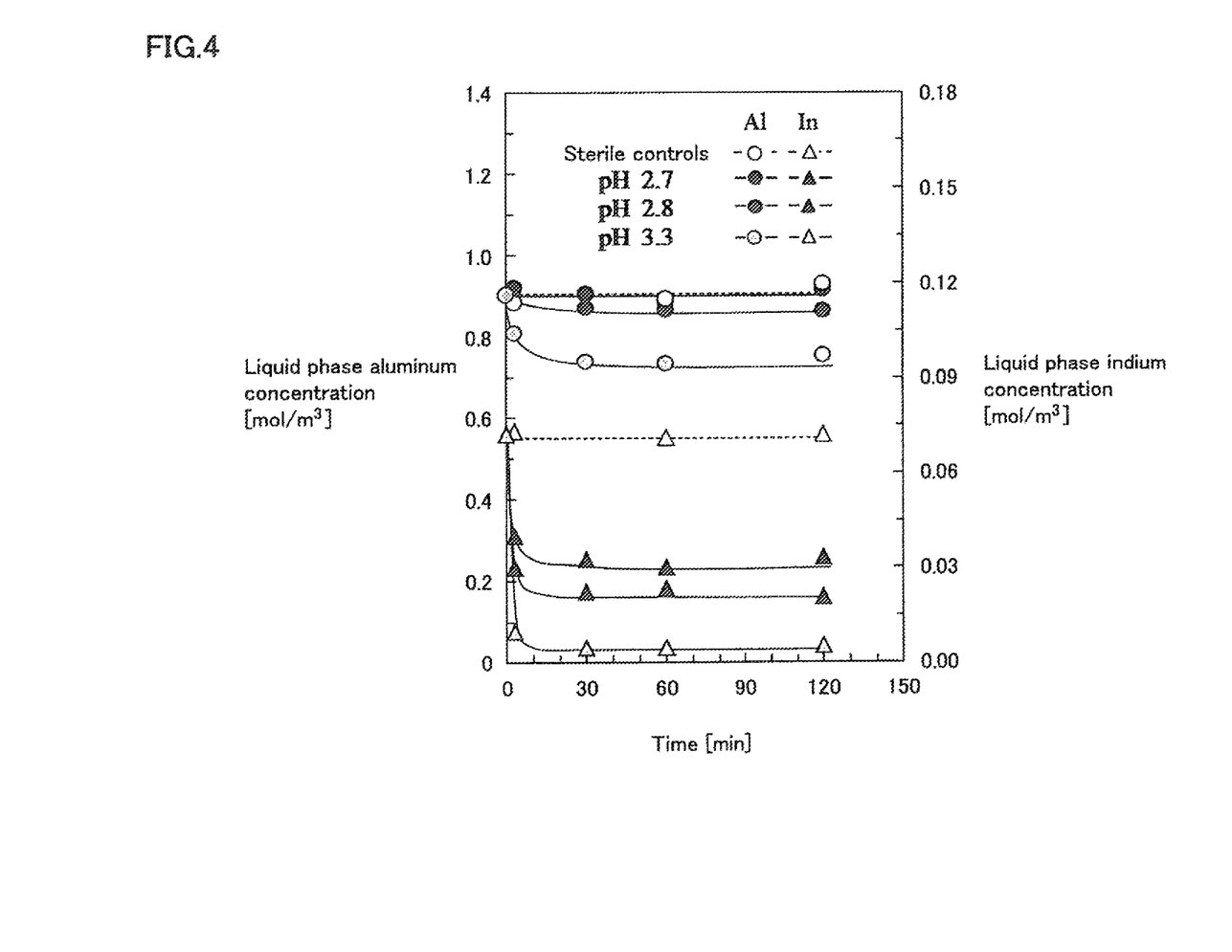
FIG. 4 is a graph showing the experimental results of Example 4.

As shown in FIG. 4, because of the adsorption by cells of *S. algae*, the concentration of In (III) ions in the liquid phase is sharply decreased with the lapse of time and the biosorption arrives at the equilibrium state by a batch process operation performed over a period of 30 minutes or less. In the case where the pH of the liquid mixture is 2.7, although the equilibrium adsorption percentage of In (III) achieved by cells of *S. algae* is 56%, it can be seen that Al (III) ions are not adsorbed to microbial cells. In the case of the solution pH of 2.8, although the In (III) equilibrium adsorption percentage increases to 69%, small amounts of Al (III) ions are also adsorbed and the Al (III) equilibrium adsorption percentage attains 4%. Furthermore, in the case of the solution pH of 3.3, the In equilibrium adsorption percentage and the Al (III) equilibrium adsorption percentage increase to 93% and 20%, respectively. The pH dependency of the metal adsorption percentage in the binary system corresponds to that in the result of the single metal ion system (FIG. 2). Thus, since the results of Example 2 reveal that the pH value at which the cell of *S. algae* acts as an adsorbing agent for In (III) ions is a pH value greater than or equal to 2.2, in the In (III)-Al (III) solution, it is thought that the preferred pH range in which only In (III) ions can be selectively adsorbed and separated using cells of *S. algae* is pH 2.2 to 3.0, and the more preferred pH range is pH 2.5 to 2.7.

In this connection, in order to enhance the adsorption percentage of In (III) ions, an experiment in which the amount of cells of *S. algae* inoculated into the In (III)-Al (III) solution is increased was also performed under the condition of the optimum pH of 2.6. As a result of allowing the cell concentration in the liquid mixture to increase from $4.0 \times 10^{15}$ to $1.0 \times 10^{16}$ cells/m$^3$, the In (III) equilibrium adsorption percentage is allowed to increase from 54% to 80%. In this case, it has been confirmed that Al (III) ions do not undergo biosorption. Thus, the operational conditions in which In (III) ions can be selectively separated at a high adsorption percentage of 80% have become clear.

Example 5

In the present example, using an LCD leachate as an object obtained from an actually used LCD, an adsorption experiment of In (III) by means of cells of *S. algae* was performed.

(Leaching Step)

First, a display (FTD-G732AS) available from BUFFALO INC. was disassembled by hand to take out a liquid crystal panel, and polarizing filters on both sides thereof were removed, after which this was ground with a hammer. The ground product was washed with ion-exchanged water and then ground so as to allow the particle diameter to be about 1 mm using a self-operating mortar to prepare a used LCD sample.

With regard to a portion of the LCD sample, the indium content was previously measured by chemical leaching. Specifically, an LCD sample was added to a 3 M aqueous hydrochloric acid solution in the same manner as that described in NPD 2, and the indium concentration in the hydrochloric acid solution (leachate) was measured using a multi-type ICP emission spectroscopic analyzer (ICPE-9000, Shimadzu Corporation). As a result of the measurement, the indium content in the LCD sample was calculated to be 0.31 mg/g. Moreover, it was also confirmed that in the leachate of the LCD sample, tin forming an oxide as ITO with indium and aluminum as a transition metal are present.

Next, by hydrothermal leaching using a dilute aqueous hydrochloric acid solution, indium was allowed to leach out from the LCD sample. That is, to an aqueous hydrochloric acid solution of 100 mol/m$^3$ (0.1M) which is a leaching agent, 0.1 g/cm$^3$-aqueous hydrochloric acid solution of the LCD sample was added and subjected to a hydrothermal treatment under the conditions of 100° C. (0.101 MPa) to 160° C. (0.618 MPa) shown in Table 1. In this case, with regard to the treatment under each hydrothermal condition, the treating time was allowed to vary between 5 and 60 minutes. The concentration of each of metals (In, Al, Sn and Sr) in an aqueous hydrochloric acid solution after a hydrothermal treatment was measured using a multi-type ICP emission spectroscopic analyzer (ICPE-9000, Shimadzu Corporation).

As a result, in all of the hydrothermal conditions, it has become apparent that leaching of In (III) is completed by a batch process operation (a hydrothermal treatment) performed over a period of 5 minutes. The relationships between the amount of each metal allowed to leach into the aqueous hydrochloric acid solution from the LCD sample in a batch process operation performed over a period of 5 minutes and the hydrothermal condition (temperature, pressure) are shown in Table 1.

TABLE 1

| Hydrothermal condition | Amount of each metal allowed to leach out from LCD sample (mg/g-LCD) | | | |
|---|---|---|---|---|
| (Temperature/Pressure) | In | Al | Sn | Sr |
| 100° C./0.101 MPa | 0.233 | 0.341 | 0.0 | 0.216 |
| 110° C./0.143 MPa | 0.271 | 0.468 | 0.0 | 0.345 |
| 120° C./0.198 MPa | 0.310 | 0.652 | 0.0 | 0.446 |
| 130° C./0.270 MPa | 0.309 | 0.822 | 0.0 | 0.506 |
| 140° C./0.361 MPa | 0.311 | 1.10 | 0.0 | 0.759 |
| 160° C./0.618 MPa | 0.312 | 2.21 | 0.0 | 1.55 |

As shown in Table 1, under the hydrothermal conditions of 120° C. (0.198 MPa) to 160° C. (0.618 MPa), the amount of indium allowed to leach out shows an almost constant value of about 0.31 mg/g-LCD. This measured value corresponds to the LCD indium content (the measured value obtained by employing an aqueous hydrochloric acid solution of 3000 mol/m$^3$) previously measured by chemical leaching. On the other hand, since the amounts of Al and Sr allowed to leach out increase with a rise in temperature and pressure, it can be seen that the optimum hydrothermal leaching condition for selectively allowing In to leach out is a condition that lies within a predetermined range including 120° C. (0.198 MPa).

In this connection, since Sn is not detected in the leachate under the conditions of the present experiment, it can be assumed that Sn is not present in the leachate. It is presumed that this is because Sn (IV) allowed to leach into the liquid phase from the LCD sample is reprecipitated as a hydroxide, for the pH of the leachate after the leaching experiment lies within the range of 1.7 to 2.0.

Moreover, though not shown in Table 1, in the hydrothermal condition of 120° C./0.198 MPa, the amount of Ca allowed to leach out was 0.677 mg/g-LCD, the amount of Mg allowed to leach out was 0.262 mg/g-LCD and the amount of Si allowed to leach out was 0.192 mg/g-LCD. In this way, Ca, Mg and Si have been allowed to leach into the aqueous hydrochloric acid solution. It has been known that these components are not adsorbed to cells of S. algae even after the separating step described below.

(Separating Step)

After the leaching step under the hydrothermal leaching condition of 120° C. (0.198 MPa), an aqueous NaOH solution was added to the aqueous hydrochloric acid solution (the LCD leachate) and the pH was adjusted to 2.6. In this connection, this pH value was set on the basis of the assumption that the pH range in which the selective adsorption of In (III) can be attained is 2.5 to 2.7 from the results of Example 2 and Example 4.

The cell suspension of S. algae was mixed with this LCD leachate, and an adsorption experiment of In (III) ions was performed by a batch process. In the liquid mixture obtained after the cell suspension was mixed, the pH was 2.6 and the cell concentration was $6.7 \times 10^{15}$ cells/m$^3$. In this connection, even in the present example, all the operations were performed under an aerobic environment (at room temperature and atmospheric pressure).

After the adsorption experiment was started (after the cell suspension was mixed), an aliquot of the liquid mixture was sampled at the end of a predetermined time (3 minutes, 30 minutes, 60 minutes and 120 minutes). The concentration of each metal (In, Al, Sn or Sr) ion in the liquid mixture sampled was measured in the same manner as that in Example 1. Moreover, the adsorption percentage of each metal ion (the decreasing percentage of each metal ion concentration to the initial concentration in the liquid mixture) was calculated. The initial concentration of each metal ion in the LCD leachate and the adsorption percentage of each metal ion at the end of 3 minutes are shown in Table 2. In this connection, the measurement results about the aliquots of the liquid mixtures sampled at the end of each of 30 minutes, 60 minutes and 120 minutes are not described in Table 2 since those are approximately the same as the result at the end of 3 minutes.

TABLE 2

|  | In | Al | Sn | Sr |
|---|---|---|---|---|
| Metal concentration in liquid phase (ppm) | 4.6 | 11.6 | 0.0 | 7.0 |
| Adsorption percentage of metal ion (%) | 70 | 4.8 | — | 1.8 |

As shown in Table 2, while the adsorption percentages of Al (III) ions and Sr (II) ions are suppressed to rates less than or equal to 4.8%, In (III) ions can be adsorbed to cells of S. algae and separated at a high adsorption percentage of 70%. In this case, the amount of In (III) adsorbed to cells of S. algae and separated attains 4.1 mg/g-dry cells with a decrease in the In (III) concentration in the liquid phase, and from the stoichiometric relationship between the number of cells and the weight of dry cells described above, the In concentration relative to dry cells attains 0.41% by weight (4100 ppm). Since the initial concentration of In (III) ions in the LCD leachate is 4.6 ppm, the In concentration rate attains about 890 (4100/4.6≈891).

As stated above, using a hydrothermal leachate as an object obtained from an LCD sample with dilute hydrochloric acid, it has been experimentally demonstrated that In (III) ions can be adsorbed to cells of S. algae at a high selectivity under the conditions of the solution pH of 2.6 and the cell concentration of $6.7 \times 10^{15}$ cells/m$^3$ to separate In (III). Furthermore, by improving the operational conditions such as allowing the cell concentration to increase, it is thought that the In (III) adsorption percentage can be enhanced to a rate greater than or equal to 70% and the In concentration rate can be enhanced to a rate greater than or equal to 890.

Example 6

Although the concentration of an aqueous hydrochloric acid solution was set to 0.1M in Example 5, in the present example, an experiment for investigating the relationship between the amounts of metals allowed to leach out in the case of allowing metals in an LCD sample to leach out by hydrothermal leaching and the hydrochloric acid concentration was performed.

That is, in the leaching step in Example 5, in the case where the hydrothermal condition was set to 120° C./0.198 MPa to perform a hydrothermal treatment over a period of 5 minutes, the amount of each metal allowed to leach out from an LCD sample when the concentration of an hydrochloric acid solution is allowed to vary between 0.01M (10 mol/m$^3$), 0.1M (100 mol/m$^3$) and 1M (1000 mol/m$^3$) was measured. The relationships between the amount of each metal allowed to leach out from the LCD sample and the hydrochloric acid concentration are shown in Table 3.

TABLE 3

| Hydrochloric acid concentration | Amount of metal allowed to leach out from liquid crystal panel (mg/g-LCD) | | | |
|---|---|---|---|---|
|  | In | Al | Sn | Sr |
| 1M | 0.314 | 1.175 | 0.0 | 0.805 |
| 0.1M | 0.310 | 0.652 | 0.0 | 0.446 |
| 0.01M | 0.017 | 0.236 | 0.0 | 0.188 |

As shown in Table 3, in the case of allowing metals in the LCD sample to leach out by hydrothermal leaching, even when the hydrochloric acid concentration in the aqueous hydrochloric acid solution to be used is lowered from 1M to 0.1M, it can be seen that the amount of In (III) allowed to leach out is kept almost unchanged and only the amounts of Al and Sr allowed to leach out are reduced substantially by half. However, when the hydrochloric acid concentration in the aqueous hydrochloric acid solution to be used is further lowered from 0.1M to 0.01 M, it can be seen that the amount of In (III) allowed to leach out, as well as the amounts of Al and Sr allowed to leach out, is reduced. From these results, it is thought that the hydrochloric acid concentration in the aqueous hydrochloric acid solution used for allowing indium to leach out from an indium-containing product is preferably set to 0.05 to 0.5 M, more preferably set to about 0.1M.

Example 7

In the present example, a test for investigating the influence of the pH on the selective adsorption of indium in an LCD leachate obtained via the leaching step from LCD was performed.

That is, the adsorption percentages of indium, aluminum and strontium by microbial cells were calculated in the same manner as that in Example 5 except that the pH of an LCD leachate after the leaching step was changed and an aliquot of the liquid mixture was sampled at the end of 120 minutes after the initiation of the adsorption experiment. In this context, the pHs of liquid mixtures immediately after adding a cell suspension to each LCD leachate that allows its pH to be changed were 2.58, 2.63, 2.64, 2.72 and 2.85. In this connection, the indium concentration, the aluminum concentration, the strontium concentration and the tin concentration in the liquid mixture immediately after the addition of a cell suspension were 6.9 ppm, 18.4 ppm, 12.3 ppm and 0.0 ppm, respectively. The resulting adsorption percentages of various metals are shown in FIG. 5.

Figure 5:
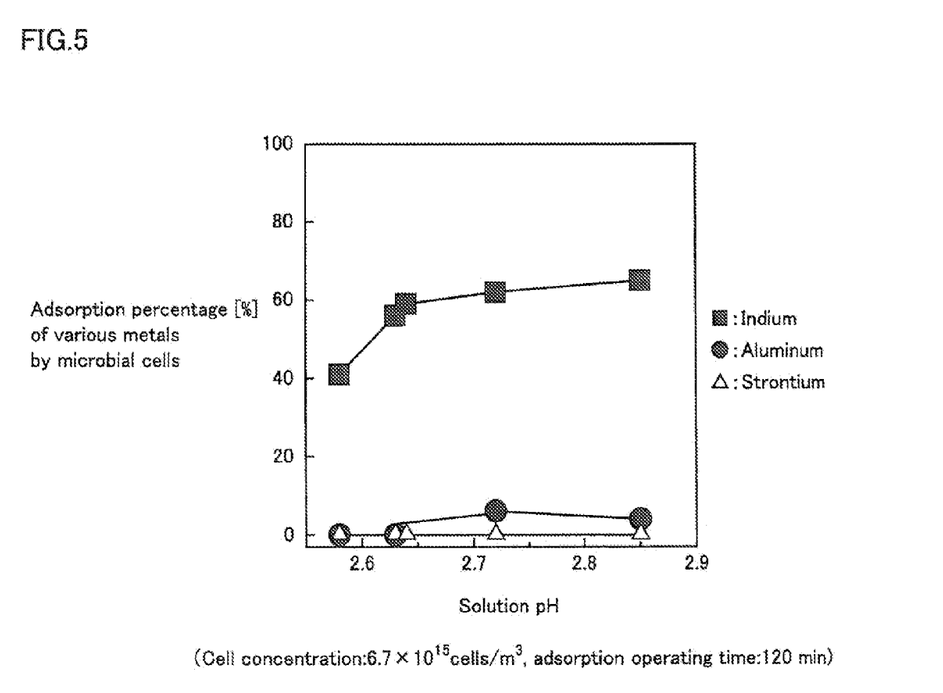
FIG. 5 is a graph showing the experimental results of Example 7.

The results shown in FIG. 5 reveal that in the case where the pH of the liquid mixture lies within the range of 2.58 to 2.85, compared to aluminum (III) ions and strontium (II) ions, the adsorption of indium (III) ions preferentially occurs. In particular, in the case where the pH of the liquid mixture is 2.63, it has been found that the adsorption of aluminum (III) ions and strontium (II) ions can be completely suppressed and only indium (III) can be selectively adsorbed with an adsorption percentage of 56%. In this connection, in the case where the pH of the liquid mixture is a pH greater than or equal to 2.72, slight adsorption of aluminum (III) ions occurs. As such, in the case where the pH of the liquid mixture lies within the range of 2.2 to 3.0, it is thought that indium (III) can be further selectively separated and recovered from the LCD leachate.

Example 8

In the present example, a test for investigating the influence of the cell concentration on the selective adsorption of indium in an LCD leachate obtained via the leaching step from LCD was performed.

That is, the adsorption percentages of indium, aluminum and strontium by microbial cells were calculated in the same manner as that in Example 5 except that the cell concentration in the liquid mixture immediately after adding a cell suspension to the LCD leachate was changed in the range of $0.5 \times 10^{16}$ to $2.4 \times 10^{16}$ cells/m$^3$ and an aliquot of the liquid mixture was sampled at the end of 120 minutes after the initiation of the adsorption experiment. In this connection, the indium concentration, the aluminum concentration, the strontium concentration and the tin concentration in the liquid mixture immediately after the addition of a cell suspension were 40.2 ppm, 107 ppm, 71.6 ppm and 0.0 ppm, respectively. The resulting adsorption percentages of various metals are shown in FIG. 6.

Figure 6:
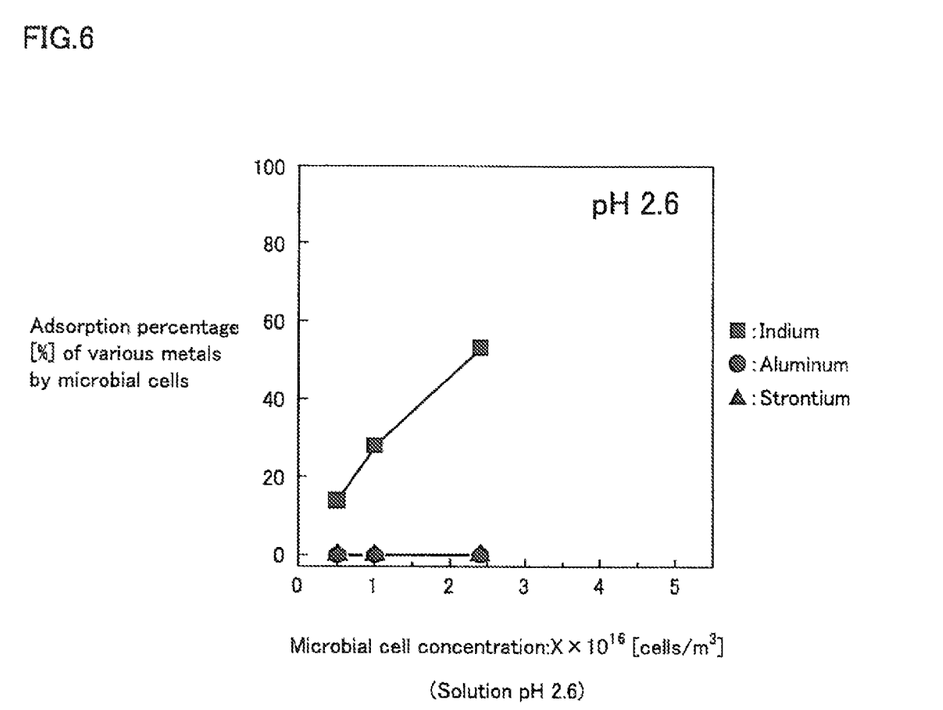
FIG. 6 is another graph showing the experimental results of Example 7.

The results shown in FIG. 6 reveal that the indium adsorption percentage increases from 14% to 54% as the cell concentration in the liquid mixture immediately after adding a cell suspension to the LCD leachate is allowed to increase from $0.5 \times 10^{16}$ to $2.4 \times 10^{16}$ cells/m$^3$.

The embodiments and examples disclosed herein are illustrative in all respects and are to be considered as being not restrictive. The scope of the present invention is shown by the claims rather than the above-mentioned description and all alterations and modifications in the meaning and the range equal to the claims are intended to be included therewithin.

The invention claimed is:

1. An indium recovery method for recovering indium from an indium-containing product, comprising a leaching step of adding an aqueous hydrochloric acid solution having a concentration of 0.05 to 0.5 M to an indium-containing product to allow indium to leach into the aqueous hydrochloric acid solution by hydrothermal leaching using the aqueous hydrochloric acid solution as a leaching agent from the indium-containing product to obtain a leachate composed of an aqueous hydrochloric acid solution containing indium, and
   a separating step of adding a microbe for adsorbing indium ions to the leachate to separate indium from the leachate.

2. The indium recovery method according to claim 1, wherein a temperature of the aqueous hydrochloric acid solution is maintained at 110 to 130° C. in the leaching step.

3. The indium recovery method according to claim 1, wherein a pressure condition in the leaching step is 0.143 to 0.270 MPa.

4. The indium recovery method according to claim 1, wherein a treating time in the leaching step is 3 to 60 minutes.

5. The indium recovery method according to claim 1, further comprising adding an alkaline material to the leachate before adding or after adding the microbe for adsorbing indium ions to thereby cause the pH of the leachate to be within the range of 2.2 to 3.0 in the separating step.

6. The indium recovery method according to claim 1, wherein the microbe for adsorbing indium ions is *Shewanella algae* or *Shewanella oneidensis*.

7. The indium recovery method according to claim 1, wherein the microbe for adsorbing indium ions is subjected to a drying treatment or is calcined after the separating step to recover indium.

* * * * *